United States Patent

Helin et al.

[11] Patent Number: 5,555,879
[45] Date of Patent: Sep. 17, 1996

[54] SAFETY MASK

[76] Inventors: Arto A. Helin, Fin-29120 Verkkoranta; Teuvo A. Mattila, Väharaumantie 82, FIN-28610 Pori, both of Finland

[21] Appl. No.: 302,916
[22] PCT Filed: Mar. 23, 1993
[86] PCT No.: PCT/FI93/00114
§ 371 Date: Nov. 15, 1994
§ 102(e) Date: Nov. 15, 1994
[87] PCT Pub. No.: WO93/18726
PCT Pub. Date: Sep. 30, 1993

[30] Foreign Application Priority Data

Mar. 23, 1992 [FI] Finland ................. U920242

[51] Int. Cl.⁶ ............................................ A62B 17/04
[52] U.S. Cl. .................. 128/201.24; 128/201.25; 128/200.28; 128/201.15
[58] Field of Search ............. 128/200.27, 200.28, 128/201.24, 201.25, 205.25, 201.15

[56] References Cited

U.S. PATENT DOCUMENTS

| 3,475,765 | 11/1969 | Zeltmann | |
| 3,629,868 | 12/1971 | Greenlee | 128/205.25 |
| 3,657,740 | 4/1972 | Cialone | 2/8 |
| 4,011,865 | 3/1977 | Morishita | 128/201.15 |
| 4,233,972 | 11/1980 | Hauff et al. | 128/200.28 |
| 4,638,146 | 1/1987 | Koyama | 219/147 |
| 4,648,394 | 3/1987 | Wise | 128/201.24 |
| 4,890,335 | 1/1990 | Crowson | 2/8 |
| 4,989,598 | 2/1991 | Berg et al. | 128/206.23 |
| 5,002,049 | 3/1991 | Knoll | 128/204.18 |
| 5,031,237 | 7/1991 | Honrud | 128/201.25 |

Primary Examiner—Aaron J. Lewis
Attorney, Agent, or Firm—Larson and Taylor

[57] ABSTRACT

A safety mask includes a hood for protecting the user's head and a blower for providing inhalation air inside the hood. An electrically driven motor operates the blower and is powered by a photoelectric cell. The photoelectric cell turns on the blower when it is illuminated by light radiation, such as from a weld torch. Because the mask need not be connected to an external power source, it is possible for an individual wearing the mask to move freely.

8 Claims, 1 Drawing Sheet

SAFETY MASK

FIELD OF THE INVENTION

The invention relates to a safety mask with a fresh air blower, the driving power of which is taken mainly from energy produced by a photoelectric cell connected to the mask.

BACKGROUND OF THE INVENTION

Previously known safety masks are of design into which air is blown by an accumulator driven blower connected to the mask, or by a blower, close to the site of the mask, from which air is conducted to the mask along hoses.

The disadvantages of these masks have been, in the first case the weight of the transportable accumulator and its need to be charged which has to be done more often for the smaller the accumulator. In the other case, the disadvantage is that the user can move freely only within the outreach of the hoses. Further, the blowing has to be switched on and off by a separate switch.

SUMMARY OF THE INVENTION

By means of a safety mask according to this invention these disadvantages are eliminated and the safety mask is characterized in that what is described in the enclosed patent claims.

The most important advantages of this invention can be considered the facts that an accumulator may not be needed at all and, in case one would like to furnish the mask with an accumulator, a small and light-weight one is sufficient. When the safety mask is used as a welding mask, the blower starts automatically upon starting to weld. The blower also stops automatically when welding is finished. Accumulator charging takes place when the mask is under sufficient illumination. While working with the safety mask, one can move freely because there are no outside connections. In addition to the electrical system of the mask, generated and maintained in this manner, an electric darkening system and even other functions of a protecting welding glass can be connected.

BRIEF DESCRIPTION OF THE DRAWINGS

In the following the invention is prescribed in detail with reference to the enclosed drawing, where.

DESCRIPTION OF THE PREFERRED EMBODIMENTS OF THE INVENTION

Figure 1:
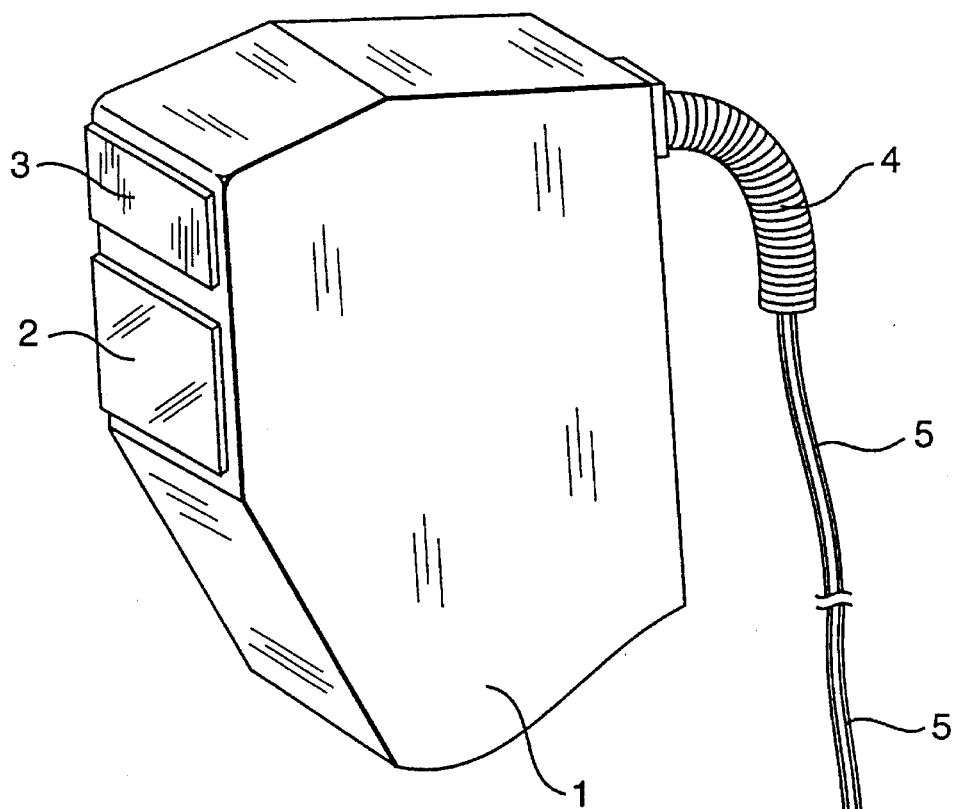
FIG. 1 is a side view of the safety mask.

FIG. 1 shows a safety mask used by a welder comprising a hoodlike part 1 protecting the user'S head from all directions. The mask has a protecting glass 2, which is conveniently made darker or becomes darker to allow the welder to safely lock at the welding arc flame. Above the protective glass there is a photoelectric cell 3, that converts light and such radiation into electric voltage. The cell 3 is directed towards the welding arc flame, so that the cell is exposed during welding to a high density of light and radiation. Conventional photoelectric cells can be used. At the back of the mask there is an inlet for an air hose 4 along which air is blown to the mask. In the example embodiment shown in figure 1 the blower is fixed on the welder's back so that the electric leads 5 from mask 1 are taken inside the hose 4 to blower 8. The blower is in a special box 6, which can also be furnished with a filter. In front of the box there is an air intake grid 7.

Figure 2:
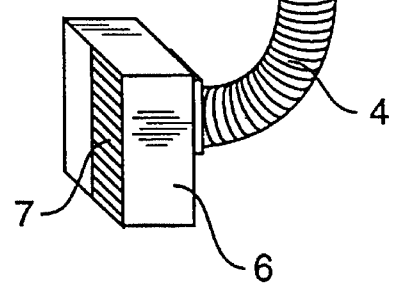
FIG. 2 is a blower arrangement of the safety mask.

FIG. 2 shows box 6 with blower 8 and accumulator 9. Electronic functions can be connected, to the box i.e. accumulator charging automation. Further, the device can contain automation which prevents blower 8 from rotating and draining the accumulator when the illumination circumstances for the accumulator are such that the blower could rotate even though a welding procedure is not in progress. The automation can also have the ability to sense the existence of the weld arc flame.

One embodiment of the device can also be the utilization of the mask during grinding. Then the illumiation may not be sufficient to rotate the blower and therefore the blower must be rotated by the accumulator alone. The device is in this case equipped with a switch to start blower 8 for operation by the accumulator.

In another embodiment of the device, the blower is fixed to the mask, so that no hoses are needed. In this case, there must be a filter associated with the mask. Also the accumulator can, in this case, be fixed to the mask if it is contained in the system.

The invention is not restricted to the enclosed embodiments but can be modified within the limits of the inventional concept determined in the patent claims. The device can be applied even to an ordinary respirator used at work in light spaces, for example, during handling of plant-protective agents at daylight with a respirator and all kinds of jobs with paints, varnishings and solvents.

We claim:

1. A safety mask comprising:

a hood for protecting a user's head;

a blower for providing inhalation air inside the hood;

an electrically driven motor for operating said blower; and driving means for driving said motor, said driving means comprising a photoelectric cell for converting energy from light radiation to electrical energy and electrical leads connecting said photoelectric cell to said motor.

2. The safety mask according to claim 1 further comprising an air hose for connecting said blower to said hood at a distance therefrom.

3. The safety mask according to claim 2 wherein said photoelectric cell is positioned on said hood and connected to said blower by electrical leads.

4. The safety mask according to claim 3 wherein said electrical leads are positioned inside said air hose.

5. The safety mask according to claim 1 wherein said hood further includes a filter and the blower is fixed directly to the safety mask.

6. The safety mask according to claim 1 wherein said driving means further comprises an accumulator for driving said motor when light radiation is less than an amount needed for said photoelectric cell to drive said motor.

7. The safety mask according to claim 6 further comprising a switch for electrically connecting said accumulator to said motor.

8. The safety mask according to claim 1 wherein said photoelectric cell has an electrical power output sufficient to convert light radiation from a welding arc to electrical energy for driving said motor.

* * * * *